(12) United States Patent
Maskara et al.

(10) Patent No.: US 8,423,140 B2
(45) Date of Patent: Apr. 16, 2013

(54) SYSTEM AND METHOD FOR DECOMPENSATION DETECTION AND TREATMENT BASED ON PATIENT HEMODYNAMICS

(75) Inventors: Barun Maskara, Blaine, MN (US); Lili Liu, Maple Grove, MN (US); Guy Alvarez, Lino Lakes, MN (US); Scott A. Meyer, Lakeville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/787,630

(22) Filed: May 26, 2010

(65) Prior Publication Data

US 2010/0305649 A1 Dec. 2, 2010

Related U.S. Application Data

(60) Provisional application No. 61/182,918, filed on Jun. 1, 2009.

(51) Int. Cl.
*A61N 1/08* (2006.01)

(52) U.S. Cl.
USPC .................................. 607/9; 607/11; 607/17

(58) Field of Classification Search ............... 607/9, 11, 607/17
See application file for complete search history.

(56) References Cited

U.S. PATENT DOCUMENTS

| | | | |
|---|---|---|---|
| 4,686,987 A | 8/1987 | Salo et al. | |
| 4,708,143 A | 11/1987 | Schroeppel | |
| 4,967,755 A | 11/1990 | Pohndorf | |
| 5,129,394 A | 7/1992 | Mehra | |
| 5,156,147 A | 10/1992 | Warren et al. | |
| 5,324,326 A | 6/1994 | Lubin | |
| 5,356,883 A | 10/1994 | Kuo et al. | |
| 5,464,434 A | 11/1995 | Alt | |
| 5,480,412 A | 1/1996 | Mouchawar et al. | |
| 5,626,623 A | 5/1997 | Kieval et al. | |
| 6,026,324 A | 2/2000 | Carlson | |
| 6,119,040 A | 9/2000 | Chirife | |
| 6,277,078 B1 | 8/2001 | Porat et al. | |
| 6,278,894 B1 | 8/2001 | Salo et al. | |

(Continued)

FOREIGN PATENT DOCUMENTS

| | | |
|---|---|---|
| EP | 0498533 | 8/1992 |
| WO | WO 0113792 | 3/2001 |
| WO | WO 2007/099533 | 9/2007 |
| WO | WO 2007/115188 | 10/2007 |

OTHER PUBLICATIONS

U.S. Appl. 12/787,868, filed May 26, 2010 to Maskara, Barun et al.

(Continued)

*Primary Examiner* — Joseph Dietrich
(74) *Attorney, Agent, or Firm* — Faegre Baker Daniels LLP

(57) ABSTRACT

A system and method for detecting and treating symptoms of early decompensation utilizing a cardiac rhythm management. The system applies an electrical stimulus to the patient's heart at a first set of pacing parameters including a lower rate limit (LRL) setting, and acquires a coronary venous pressure (CVP) signal from a pressure sensor implanted in a coronary vein of the patient. An average coronary venous end diastolic pressure (CV-EDP) value is calculated from the CVP signal. The system monitors the average CV-EDP value over a predetermined interval, and dynamically adjusts the LRL setting responsive to the detection of a first or a second predetermined event based on the average CV-EDP value.

10 Claims, 6 Drawing Sheets

U.S. PATENT DOCUMENTS

| | | |
|---|---|---|
| 6,366,811 B1 | 4/2002 | Carlson et al. |
| 6,580,946 B2 | 6/2003 | Struble |
| 6,666,826 B2 | 12/2003 | Salo et al. |
| 6,839,593 B1 | 1/2005 | Sun et al. |
| 6,892,095 B2 | 5/2005 | Salo |
| 6,934,586 B2 | 8/2005 | Struble et al. |
| 6,944,499 B2 | 9/2005 | Tang et al. |
| 6,945,939 B2 | 9/2005 | Turcott |
| 6,970,742 B2 | 11/2005 | Mann et al. |
| 7,062,323 B2 | 6/2006 | Carlson et al. |
| 7,195,594 B2 | 3/2007 | Eigler et al. |
| 7,198,603 B2 | 4/2007 | Penner et al. |
| 7,200,439 B2 | 4/2007 | Zdeblick et al. |
| 7,206,637 B2 | 4/2007 | Salo |
| 7,233,821 B2 | 6/2007 | Hettrick et al. |
| 7,269,460 B2 | 9/2007 | Chinchoy |
| 7,272,443 B2 | 9/2007 | Min et al. |
| 7,389,142 B2 | 6/2008 | Holmstrom |
| 7,409,244 B2 | 8/2008 | Salo et al. |
| 7,457,663 B2 | 11/2008 | Kalgren et al. |
| 2001/0010009 A1 | 7/2001 | Bakels et al. |
| 2002/0188329 A1 | 12/2002 | Struble |
| 2003/0074029 A1 | 4/2003 | Deno et al. |
| 2003/0130581 A1 | 7/2003 | Salo et al. |
| 2003/0181938 A1 | 9/2003 | Roth et al. |
| 2003/0204209 A1 | 10/2003 | Burnes et al. |
| 2004/0138571 A1 | 7/2004 | Salo et al. |
| 2004/0230131 A1 | 11/2004 | Kassab et al. |
| 2005/0137635 A1 | 6/2005 | Molin et al. |
| 2006/0089679 A1 | 4/2006 | Zhu et al. |
| 2006/0247702 A1 | 11/2006 | Stegemann et al. |
| 2006/0271121 A1 | 11/2006 | Ding |
| 2006/0276849 A1 | 12/2006 | Carlson et al. |
| 2006/0293714 A1 | 12/2006 | Salo et al. |
| 2007/0088221 A1 | 4/2007 | Stahmann |
| 2007/0112388 A1 | 5/2007 | Salo |
| 2007/0142732 A1 | 6/2007 | Brockway et al. |
| 2007/0149890 A1 | 6/2007 | Li et al. |
| 2007/0239218 A1 | 10/2007 | Carlson et al. |
| 2007/0239219 A1 | 10/2007 | Salo et al. |
| 2007/0249945 A1 | 10/2007 | Li et al. |
| 2008/0082135 A1 | 4/2008 | Arcot-Krishnamurthy et al. |
| 2008/0281367 A1 | 11/2008 | Zhang et al. |
| 2009/0149766 A1 | 6/2009 | Shuros et al. |
| 2009/0204163 A1 | 8/2009 | Shuros et al. |
| 2010/0042175 A1 | 2/2010 | Liu et al. |
| 2010/0305635 A1 | 12/2010 | Liu et al. |
| 2010/0305650 A1 | 12/2010 | Maskara et al. |

OTHER PUBLICATIONS

Benchimol, Alberto et al., "Hemodynamic consequences of atrial and ventricular pacing in patients with normal and abnormal hearts", American Journal of Medicine, vol. 39, No. 6, Dec. 1, 1965, 911-922.

International Search Report and Written Opinion issued in PCT/US2010/036174, mailed Jul. 21, 2010, 15 pages.

International Search Report and Written Opinion issued in PCT/US2010/036137, mailed Oct. 28, 2010, 16 pages.

International Search Report and Written Opinion issued in PCT/US2010/035949, dated Oct. 26, 2010, 18 pages.

International Search Report and Written Opinion issued in PCT/US2010/036137, mailed Oct. 28, 2010.

International Search Report and Written Opinion issued in PCT/US2008/080778, dated Feb. 12, 2009.

SYSTEM AND METHOD FOR DECOMPENSATION DETECTION AND TREATMENT BASED ON PATIENT HEMODYNAMICS

CROSS-REFERENCE TO RELATED APPLICATIONS

This application claims the benefit under 35 U.S.C. §119 of U.S. Provisional Application No. 61/182,918, filed Jun. 1, 2009, entitled "System and Method for Decompensation Detection and Treatment Based on Patient Hemodynamics," which is incorporated herein by reference for all purposes.

This application is also related to co-pending and commonly assigned U.S. Patent Publication No. 2010/0305650, filed on May 26, 2010, and entitled "System and Method for Pacing Rate Control Utilizing Patient Hemodynamic Status Information," which is incorporated herein by reference for all purposes.

TECHNICAL FIELD

The present invention relates to medical devices and methods for cardiac rhythm management. More specifically, the present invention relates to systems and methods for automatically adjusting the operating parameters of a cardiac pacemaker or cardiac resynchronization therapy system.

BACKGROUND

Implantable cardiac rhythm management (CRM) systems, including pacemakers, implantable cardioverter/defibrillators (ICDs), and cardiac resynchronization therapy (CRT, CRT-D) devices have been used to deliver effective treatment to patients with serious cardiac arrhythmias. In particular, rate adaptive pacing systems are known which utilize data obtained from various implanted sensors to adjust pacing parameters in response to increased patient demand.

SUMMARY

The present invention, in one embodiment, is a method of operating an implanted cardiac rhythm management system in a patient. The method comprises applying an electrical stimulus to the patient's heart at a first set of pacing parameters including a lower rate limit (LRL) setting. The method further comprises acquiring a coronary venous pressure (CVP) signal from a pressure sensor implanted in a coronary vein of the patient. An average coronary venous end diastolic pressure (CV-EDP) value is calculated from the CVP signal, and the average CV-EDP value is monitored over a predetermined interval. The method further comprises dynamically adjusting the LRL setting responsive to the detection of a first or a second predetermined event based on the average CV-EDP value.

In another embodiment, the present invention is a method of operating an implanted cardiac rhythm management system in a patient, the method comprising applying an electrical stimulus to the patient's heart at a first set of pacing parameters including an LRL setting, acquiring a CVP signal from a pressure sensor implanted in a coronary vein of the patient, and calculating a baseline CV-EDP value from the CVP signal corresponding to a first interval. The average CV-EDP values are monitored over a predetermined time interval subsequent to the first interval. The method further comprises comparing each of the average CV-EDP values to the baseline CV-EDP value, and automatically increasing the LRL setting in response to a difference ($\Delta$CV-EDP) between at least one of the average CV-EDP values and the baseline average CV-EDP value exceeding a predetermined threshold. The method further comprises subsequently automatically reducing the LRL setting upon detecting a predetermined event.

In yet another embodiment, the present invention is an implantable rate adaptive cardiac rhythm management system configured for applying a pacing stimuli to a patient's heart, the pacing stimuli defined by pacing parameters including a pacing rate and an LRL setting. The system comprises a plurality of implantable medical electrical leads and an implantable pulse generator. The leads are configured to sense cardiac electrical activity and to deliver the pacing stimuli, at least one of the leads being configured for chronic implantation within a coronary vein of the patient's heart and including a pressure sensor configured to generate a coronary venous pressure (CVP) signal indicative of fluid pressure within the coronary vein. The pulse generator is operatively coupled to the leads and is configured to generate the pacing stimuli, and includes a control system configured to acquire the CVP signal from the pressure sensor, calculate an average coronary venous end diastolic pressure (CV-EDP) value from the CVP signal, and monitor the calculated average CV-EDP value over a predetermined interval. The control system is further configured to dynamically adjust the LRL setting responsive to the detection of a first or a second predetermined event based on the calculated average CV-EDP value.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
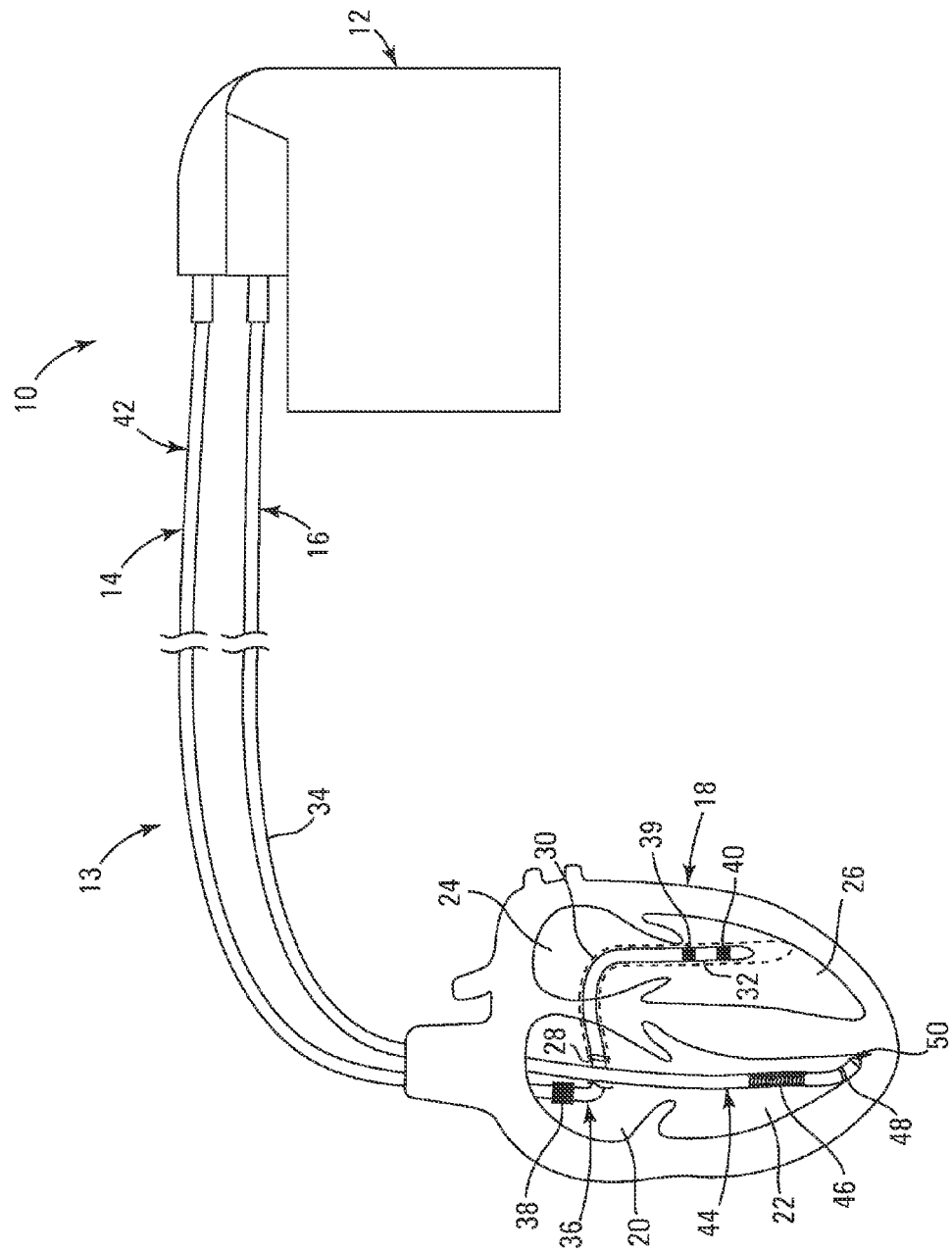
FIG. 1 is a schematic illustration of an implantable cardiac rhythm management (CRM) system according to one embodiment of the present invention in a deployed configuration.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic drawing of an implantable cardiac rhythm management (CRM) system 10 according to one embodiment of the present invention, shown in a deployed state. As shown in FIG. 1, the CRM system 10 includes a pulse generator 12 coupled to a cardiac lead system 13 including a pair of medical electrical leads 14, 16 deployed in a patient's heart 18, which includes a right atrium 20 and a right ventricle 22, a left atrium 24 and a left ventricle 26, a coronary sinus ostium 28 in the right atrium 20, a coronary sinus 30, and various coronary veins including an exemplary branch vessel 32 off of the coronary sinus 30.

As discussed in detail below, the CRM system 10 is advantageously configured to treat cardiac arrhythmias in a patient suffering from CHF. More specifically, the CRM system 10 is configured to adjust pacing parameters to relieve symptoms associated with early decompensation resulting from CHF. The CRM system 10 utilizes hemodynamic performance information based on the output from implanted pressure sensors to diagnose medical conditions, such as the onset of early decompensation resulting from CHF, and to optimize the pacing system parameters to treat CHF-related symptoms. In various embodiments, the pressure sensors provide information that is indicative of or correlates closely to the patient's left ventricular pressure (LVP), which is a useful measure as an indicator of cardiac function in patients suffering from CHF.

As shown in FIG. 1, the lead 14 includes a proximal portion 42 and a distal portion 36, which as shown is guided through the right atrium 20, the coronary sinus ostium 28 and the coronary sinus 30, and into the branch vessel 32 of the coronary sinus 30. The distal portion 36 further includes pressure sensors 38, 39, and an electrode 40. As shown, the pressure sensor 39 and the electrode 40 are positioned on the lead 14 such that, when implanted, they are both located within the branch vessel 32. As further shown, the pressure sensor 38 is positioned on the lead 14 such that, when implanted, it is located within the right atrium 20. Alternatively, the additional pressure sensor 38 could be located in the coronary sinus 30. The illustrated position of the lead 14 may be used for delivering a pacing and/or defibrillation stimulus to the left side of the heart 18. Additionally, the lead 14 may also be partially deployed in other regions of the coronary venous system, such as in the great cardiac vein or other branch vessels for providing therapy to the left side or right side of the heart 18.

In the illustrated embodiment, the electrode 40 is a relatively small, low voltage electrode configured for sensing intrinsic cardiac electrical rhythms and/or delivering relatively low voltage pacing stimuli to the left ventricle 26 from within the branch coronary vein 32. In various embodiments, the lead 14 can include additional pace/sense electrodes for multi-polar pacing and/or for providing selective pacing site locations.

As further shown, in the illustrated embodiment, the lead 16 includes a proximal portion 34 and a distal portion 44 implanted in the right ventricle 22. In other embodiments, the CRM system 10 may include still additional leads, e.g., a lead implanted in the right atrium 20. The distal portion 44 further includes a flexible, high voltage electrode 46, a relatively low-voltage ring electrode 48, and a low voltage tip electrode 50 all implanted in the right ventricle 22 in the illustrated embodiment. The high voltage electrode 46 has a relatively large surface area compared to the ring electrode 48 and the tip electrode 50, and is thus configured for delivering relatively high voltage electrical stimulus to the cardiac tissue for defibrillation/cardioversion therapy, while the ring and tip electrodes 48, 50 are configured as relatively low voltage pace/sense electrodes. The electrodes 48, 50 provide the lead 16 with bi-polar pace/sense capabilities.

In various embodiments, the lead 16 includes additional defibrillation/cardioversion and/or additional pace/sense electrodes positioned along the lead 16 so as to provide multi-polar defibrillation/cardioversion capabilities. In one exemplary embodiment, the lead 16 includes a proximal high voltage electrode in addition to the electrode 46 positioned along the lead 16 such that it is located in the right atrium 20 (and/or superior vena cava) when implanted. Additional electrode configurations can be utilized with the lead 16. In short, any electrode configuration can be employed in the lead 16 without departing from the intended scope of the present invention.

In various embodiments, the lead 14 can be configured according to the various embodiments described in co-pending and commonly assigned U.S. Provisional Patent Application 61/088,270 titled "Implantable Lead and Coronary Venous Pressure Sensor Apparatus and Method" to Liu, et al. or commonly assigned U.S. Pat. No. 7,409,244 titled "Method and Apparatus for Adjusting Interventricular Delay Based on Ventricular Pressure," to Salo, et al., the disclosures of which are incorporated herein by reference in their entireties. In other embodiments, the lead 14 with pressure sensor 39 and/or 38 can have other suitable configurations.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient suitable for treating cardiac tachyarrhythmias. In various embodiments, the pulse generator 12 is a pacemaker, an implantable cardioverter defibrillator (ICD) or a cardiac resynchronization (CRT) device configured for bi-ventricular pacing and including defibrillation capabilities (i.e., a CRT-D device). While not shown in FIG. 1, the pulse generator 12 includes hardware, software, and circuitry operable as a detection/energy delivery system configured to receive cardiac rhythm signals from the lead electrode(s) 40, 48, 50 and pressure signals from the pressure sensor(s) 38, 39, and also to deliver a therapeutic electrical stimulus to the electrodes 40, 48, 50.

In various embodiments, the CRM system 10 further includes an additional lead deployed in the right atrium 20, which lead may include one or more additional electrodes sensing intrinsic cardiac signals and/or delivering electrical stimuli to the cardiac tissue within the right atrium 20.

The pressure sensor 39 is operable to sense and to generate an electrical signal representative of a fluid pressure parameter within the coronary vein 32 in which it is implanted. The pressure sensor 39 can be any device, whether now known or later developed, suitable for sensing pressure parameters within the coronary venous system and generating and transmitting a signal indicative of such pressure parameters to another device, e.g., the pulse generator 12. In various embodiments, the pressure sensor 39 is configured to sense and generate a signal indicative of hydrostatic pressure within the coronary vein. In various embodiments, the pressure sensor 39 can be a micro-electrical-mechanical system (MEMS) device, which utilizes semiconductor techniques to build microscopic mechanical structures in a substrate made from silicon or similar materials. In various embodiments, the pressure sensor 39 can include a micro-machined capacitive or piezoresistive sensor exposed to the bloodstream. Other pressure sensor technologies, such as resistive strain gages, are known in the art and can also be employed as a pressure sensor 39.

In other exemplary embodiments, the pressure sensor 39 can include one or more piezoelectric elements. Such piezoelectric elements are configured to flex and/or deflect in response to changes in pressure within the coronary vein in which it is implanted, and to generate an output current or voltage proportional to the corresponding pressure change. In such embodiments, the pressure sensor 39 may advantageously be configured to sense fluid characteristics indicative of changes in coronary venous pressure parameters, e.g., coronary venous end diastolic pressure, which in turn can be monitored over time. In addition, the pressure sensor 38 can be used to sense right atrial pressure, which can be a useful surrogate for central venous pressure and can be monitored over time to provide an indication of right side heart decompensation.

Figure 2:
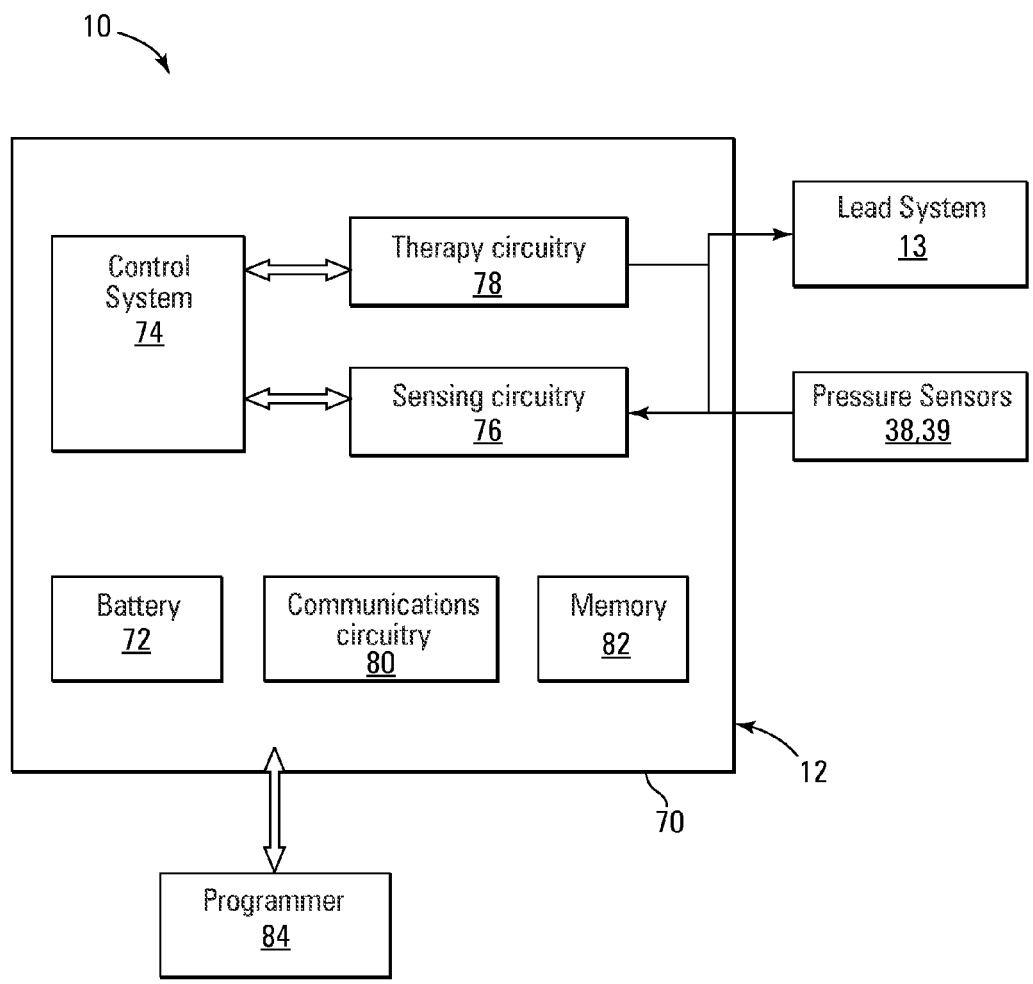
FIG. 2 is a block diagram illustrating functional components of the implantable medical system of FIG. 1.

FIG. 2 is a schematic functional block diagram of an embodiment of the implantable medical system 10. As shown in FIG. 2, the system 10 is divided into functional blocks. The illustrated configuration is exemplary only, and there exist many possible configurations in which these functional blocks can be arranged. The example depicted in FIG. 2 is one possible functional arrangement. The system 10 includes circuitry for receiving cardiac electrical signals, coronary venous pressure signals, and in some embodiments, right atrial pressure signals from the heart 18 and generating and delivering electrical energy in the form of pace pulses or cardioversion/defibrillation pulses to the heart 18.

As discussed above, the cardiac lead system 13, which includes the leads 14, 16 may be implanted so that the cardiac electrodes 40, 48, 50 (see FIG. 1) contact heart tissue. The cardiac electrodes of the lead system 13 sense cardiac signals associated with electrical activity of the heart. In addition, the pressure sensors 38, 39 on the lead 14 detect and generate pressure signals indicative of blood pressure within the right atrium 20 and coronary vein 32, respectively. The sensed cardiac signals and pressure signals are transmitted to the pulse generator 12 through the lead system 13. The cardiac electrodes and lead system 13 may be used to deliver electrical stimulation generated by the pulse generator 12 to the heart to mitigate various cardiac arrhythmias. The pulse generator 12, in combination with the cardiac electrodes and the lead system 13, may detect cardiac signals and deliver therapeutic electrical stimulation to any of the left and right ventricles and left and right atria, for example.

As shown, the pulse generator 12 includes circuitry encased in a hermetically sealed housing 70 suitable for implanting in a human body. Power is supplied by a battery 72 that is housed within the housing 70. In one embodiment, the pulse generator circuitry is a programmable microprocessor-based system, including a control system 74, sensing circuitry 76, therapy circuitry 78, communications circuitry 80, and memory 82. The memory 82 may be used, for example, to store programmed instructions for various pacing and defibrillation therapy and sensing modes, and also data associated with sensed cardiac signals or other physiologic data, e.g., blood pressure. The parameters and data stored in the memory 82 may be used on-board for various purposes and/or transmitted via telemetry to an external programmer unit 84 or other patient-external device, as desired. In various embodiments, the stored data can be uploaded by a clinician and/or transmitted over an advanced patient management (APM) system, such as the LATITUDE® system marketed by Boston Scientific Corporation.

The communications circuitry 80 allows the pulse generator 12 to communicate with the external programmer unit 84 and/or other patient-external system(s). In one embodiment, the communications circuitry 80 and the programmer unit 84 use a wire loop antenna and a radio frequency telemetric link to receive and transmit signals and data between the programmer 84 and communications circuitry 80. In this manner, programming commands may be transferred to the pulse generator 12 from the programmer 84 during and after implantation. In addition, stored cardiac data may be transferred to the programmer unit 84 from the pulse generator 12, for example.

The sensing circuitry 76 detects cardiac signals sensed at the cardiac electrodes 40, 48, 50, as well as blood pressure signals generated by the pressure sensors 38, 39, and signals from other implanted sensors (e.g., activity sensors providing information relating to the patient's physical activity and associated metabolic demand). The sensing circuitry 76 may include, for example, amplifiers, filters, ND converters and other signal processing circuitry. Cardiac signals and pressure signals processed by the sensing circuitry may be communicated to the control system 74.

The therapy circuitry 78 is controlled by the control system 74 and may be used to deliver therapeutic stimulation pulses to the heart through one or more of the cardiac electrodes, according to a pre-established pacing regimen under appropriate conditions. Thus, in various embodiments, the therapy circuitry 78 is configured to deliver pacing stimuli to the right side and, in the case of a CRT or CRT-D system such as the CRM system 10, also to the left side of the heart 18. In various embodiments, the therapy circuitry 78 is also configured to deliver anti-tachycardia therapy stimuli to the ventricles and/or the atria. Such therapies may include, without limitation, relatively low-energy anti-tachycardia pacing pulses as well as high-energy shocks to treat and disrupt ventricular fibrillation episodes.

The control system 74 is used to control various subsystems of the pulse generator 12, including the therapy circuitry 78 and the sensing circuitry 76. The control system 74 performs various functions, including, for example, arrhythmia analysis and therapy selection. An arrhythmia analysis section of the control system 74 may compare signals detected through the sensing circuitry 76 to detect or predict various cardiac arrhythmias, and to assist selection of appropriate therapies for the patient. In general, the control system 74 controls therapy delivery according to pacing parameters programmed by the clinician either at implantation or thereafter.

As discussed above, the CRM system 10 utilizes hemodynamic performance information based on the output from the implanted pressure sensors, e.g., pressure sensors 39 and/or 38, to diagnose medical conditions including the onset of early decompensation resulting from CHF, and optimizes the pacing system parameters to treat CHF-related symptoms.

In particular, as discussed in detail below, one pacing parameter that is dynamically adjusted by the CRM system 10 to treat symptoms of early decompensation is the lower rate limit (LRL). The LRL is a programmed parameter defining the pacing rate (e.g., number of pulses per minute) at which the pulse generator 12 will deliver pacing stimuli in the absence of sensed intrinsic cardiac activity. In other words, unless the CRM system 10 senses cardiac activity or metabolic demand dictating stimulating at a different rate, the pulse generator 12 will deliver pacing stimuli at the LRL. According to various embodiments of the present invention, the LRL can be automatically adjusted by the control system 74 upon detecting the onset of decompensation so as to cause the CRM system 10 to pace the heart at an increased rate, thereby facilitating removal of fluid accumulated in the patient's heart and/or lungs.

As further discussed above, LVP is a useful indicator of hemodynamic performance in patients with CHF, and can provide an indication as to worsening hemodynamic conditions, including the onset of early decompensation in CHF patients. In particular, the left ventricular end diastolic pressure (LV-EDP) is an especially important measure used to evaluate hemodynamic state. That is, an increase in LV-EDP over time can be a reliable indicator of symptoms associated with early decompensation caused by CHF, e.g., accumulation of blood or other fluid in the heart chambers or the lungs as a result of the reduced hemodynamic performance of the heart 18 caused by CHF.

Notwithstanding the usefulness of LVP in early decompensation detection and treatment, obtaining direct LV pressure information chronically is both technically and clinically challenging. As discussed in detail below, however, LV-EDP (or other LVP-derived parameters such as LV systolic pressure (LV-SP), mean LVP, and LV dp/dt) can be estimated utilizing pressure data obtained from within a coronary vein without requiring direct pressure readings from the left ventricle or left atrium. That is, in various embodiments, coronary venous pressure (CVP) is chronically sensed using implanted pressure sensors and is utilized as a surrogate for direct LVP measurement.

Figure 3:
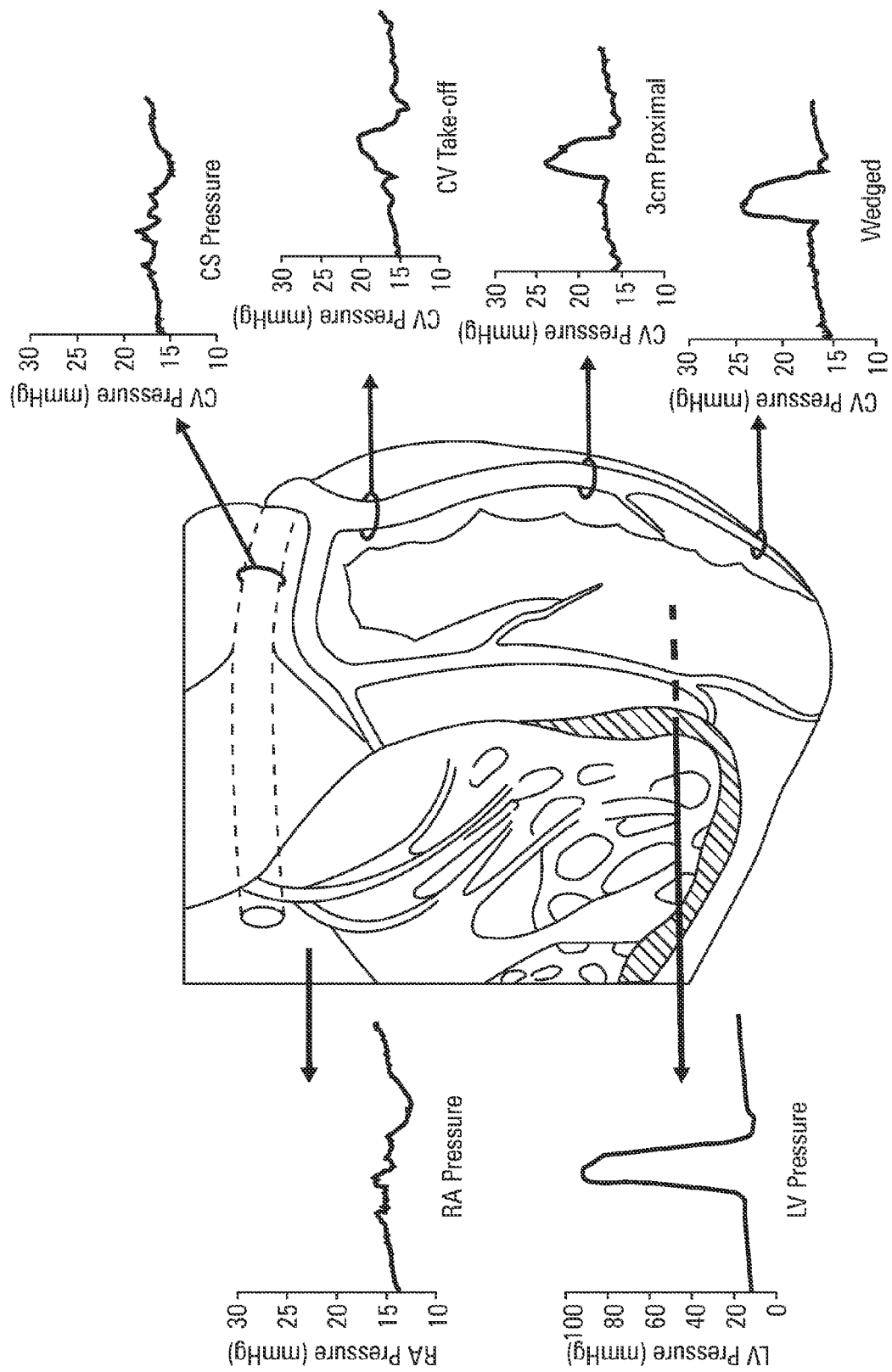
FIG. 3 is an illustration of coronary venous system pressure waveforms that can be obtained utilizing the CRM system of FIG. 1.

Referring back to FIG. 1, the pressure sensors 38, 39 are configured to detect and generate pressure signals representative of fluid pressure within the right atrium 20 and the coronary vein 36, respectively. From these pressure signals, pressure waveforms can be derived and evaluated by the sensing circuitry 76 and the control system of the pulse generator 12. FIG. 3 illustrates pressure waveforms obtained from the right atrium (RA), left ventricle (LV), coronary sinus (CS) and various locations in a coronary vein (CV) in an exemplary animal study. As shown, the coronary venous pressure (CVP) waveform takes on the same general shape as the LV waveform, particularly where the CVP is taken from a location lower in the coronary vein, i.e., as indicated by the "Wedged" (apical two-thirds) CV pressure graph.

Figure 4:
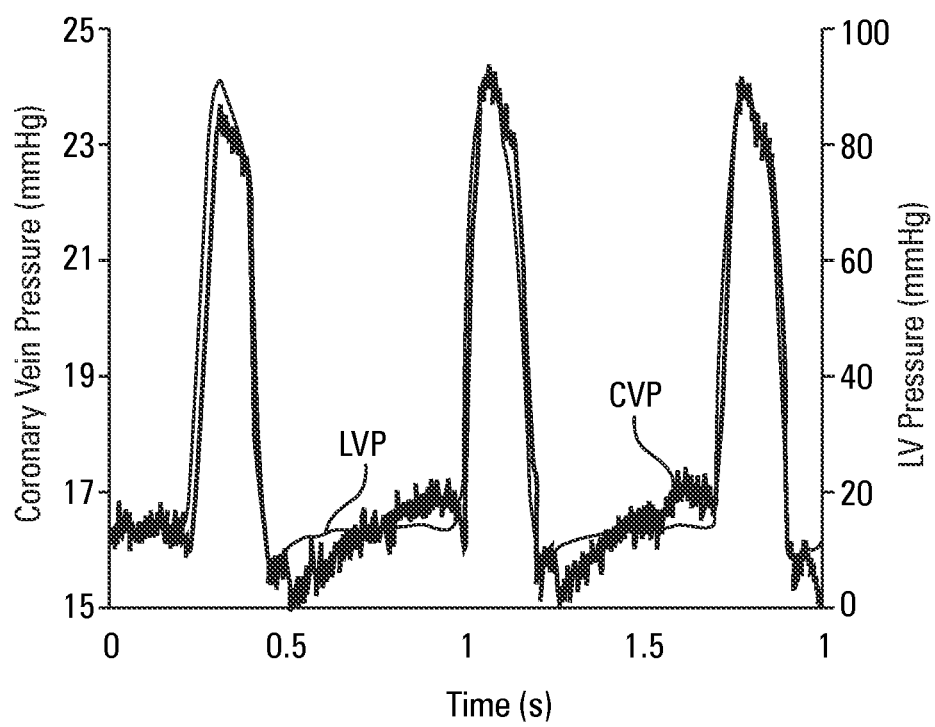
FIG. 4 is an illustration depicting a coronary venous pressure waveform and corresponding left ventricular pressure waveform.

FIG. 4 is an illustration depicting a CVP waveform and a corresponding LVP waveform also obtained in an exemplary animal study. As can be seen in FIG. 4, the CVP and LVP waveforms correlate closely to one another. Thus, in view of the close correlation between coronary venous pressure and LV pressure, CVP can function as a surrogate for LVP in the CRM system 10, which can then derive one or more CVP indexes that closely correlate to corresponding LVP indexes, and can thus be utilized in the same manner as the LVP indexes to adaptively adjust pacing parameters, e.g., pacing rate limits such as the lower rate limit (LRL), in response to changes in the patient's hemodynamic status.

Thus, from FIG. 4, it can be seen that LV-EDP can be estimated based on CVP signals obtained from the pressure sensor 39 implanted in the coronary vein 32, and optionally, the pressure sensor 38 implanted in the right atrium (or the coronary sinus). Additionally, changes in CV end diastolic pressure (CV-EDP) over time will correlate with changes in LV-EDP. Thus, hemodynamic performance information that can be derived from changes in LV-EDP over time can also be derived by monitoring changes in CV-EDP, which as discussed above, can be directly calculated based on CVP signals from the implanted pressure sensors. As further discussed above, one important diagnostic application of LV-EDP changes (and thus, CV-EDP changes as well) is to detect the onset of early decompensation in CHF patients, which can be detected based on increased LV-EDP caused by the accumulation of fluid in the patient's heart and lungs.

Figure 5:
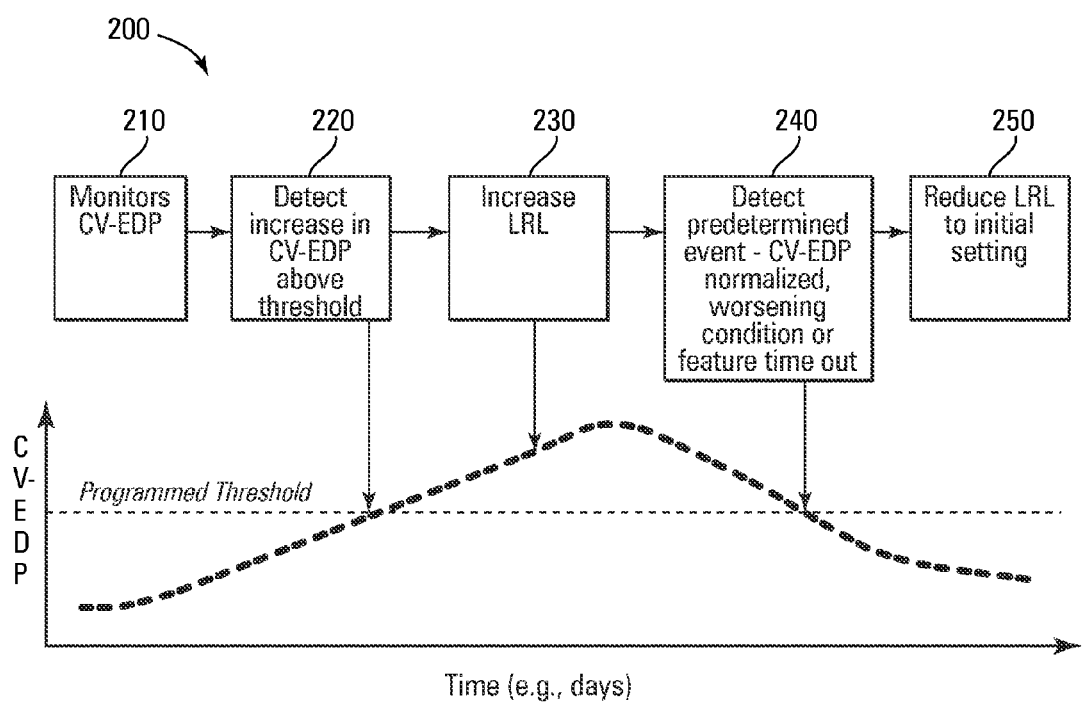
FIG. 5 is a diagram illustrating an exemplary method of operating the CRM system of FIG. 1 to treat symptoms associated with CHF according to one embodiment of the present invention.

FIG. 5 is a diagram graphically illustrating an exemplary method 200 of treating symptoms associated with CHF using the CRM system 10 according to one embodiment of the present invention. As shown in FIG. 5, the control system 74 of the CRM system 10 monitors CV-EDP calculated from the output based on the output of the implanted pressure sensor 39 (block 210). The control system 74 then detects changes in the CV-EDP, and in particular, increases in the CV-EDP above a programmed threshold value indicative of early decompensation (block 220).

Upon detecting a CV-EDP increase above the programmed threshold, the control system 74 then increases the LRL above the previously programmed value, thereby increasing the rate at which the heart 18 will be paced in the absence of sensed intrinsic events (block 230). Accordingly, by pacing at the corresponding elevated rate, the CRM system 10 facilitates removal of blood and other fluid accumulated in the patient's heart and/or lungs, thus relieving the symptoms associated with this fluid accumulation.

As further shown in FIG. 5, the control system 74 of the CRM system 10 will continue to monitor CV-EDP during the period of elevated pacing/heart rate resulting from the increase in LRL until one or more predetermined events is detected (block 240). In the illustrated embodiment, upon detection of one of the predetermined events, the control system 74 will return the LRL to its original settings (block 250). Exemplary predetermined events that will trigger this step include the CV-EDP returning back to a pre-established value, or alternatively, to a value equal to or below the programmed threshold value for triggering the LRL increase. Another event that may trigger the reduction in the LRL is the passage of a prescribed time limit for pacing at the elevated rate where the CV-EDP has not fully returned to a value below the programmed threshold. In still another embodiment, the LRL may be reduced upon a detection by the CRM system 10, based on the CV-EDP trend, of worsening hemodynamic conditions.

In various embodiments, feedback in the form of alerts or other information regarding sensed events and/or CRM system 10 operating parameters may be transmitted over an APM system to a physician or other caregiver.

The particular CVP parameters calculated and monitored can be any parameters useful for providing an indication of the patient's hemodynamic state, and in particular, for identifying the onset of symptoms associated with early decompensation. As discussed above, increases in CV-EDP provides one such useful indicator of symptoms of early decompensation. In various embodiments, the CRM system 10 is configured to calculate average CV-EDP values over predetermined intervals, e.g., a predetermined time period or a predetermined number of beats or cardiac cycles. For example, in one embodiment, the CRM system 10 generates a CVP waveform based on the CVP signal and calculates an average CV-EDP value over a predetermined interval based on the CVP waveform. In one embodiment, the CV-EDP value monitored is a rolling average CV-EDP value, which can be monitored by the CRM system 10 over time. Thus, as shown in FIG. 5, a trend in the average CV-EDP over time is monitored by the control system 74, and this trend provides the input for triggering the LRL increase by the control system 74. In still other embodiments, other CVP parameters may be monitored by the CRM system 10.

Figure 6:
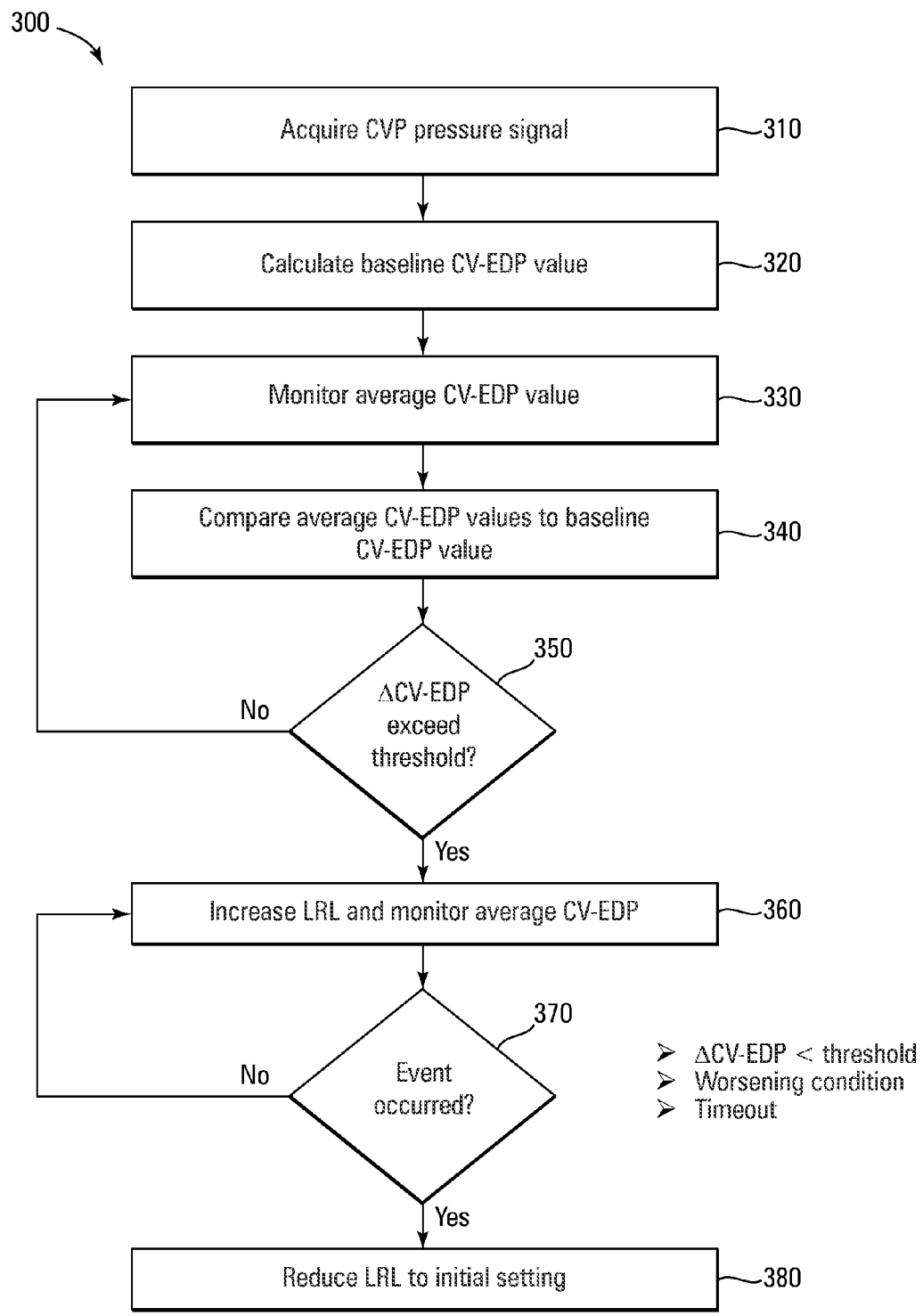
FIG. 6 is a flow chart illustrating a method of operating the CRM system of FIG. 1 to treat symptoms associated with CHF according to one embodiment of the present invention.

FIG. 6 is a flow chart illustrating a method 300 of operating the CRM system 10 to treat symptoms associated with CHF according to one embodiment of the present invention. The method 300 of FIG. 6 contemplates that the CRM system 10 is implanted and programmed to pace at an initial set of pacing parameters including an initial LRL. As shown in FIG. 6, the method 300 includes acquiring a CVP signal from the implanted pressure sensors, e.g., the pressure sensor 39 of FIG. 1 (block 310). From the pressure signal, the control system 74 of the CRM system 10 calculates a baseline CV-EDP value (block 320). In one embodiment, this baseline CV-EDP value may be based on a single measurement at a predetermined time. Alternatively, the baseline CV-EDP value may be an average CV-EDP value over a predetermined sampling interval.

As further shown in FIG. 6, the control system 74 subsequently monitors average CV-EDP values (block 330), and compares the average CV-EDP values to the baseline CV-EDP value (block 340). Here again, the average CV-EDP values may constitute a series of rolling average CV-EDP values each calculated for a predetermined time period or number of beats/cycles.

As shown, in comparing the average CV-EDP values to the baseline CV-EDP value, the control system 74 determines whether the difference ($\Delta$CV-EDP) between at least one of the average CV-EDP values and the baseline average CV-EDP value exceeds a predetermined threshold amount (block 350). If not, the control system 74 will continue to monitor the average CV-EDP values and compare them to the baseline CV-EDP value. If, however, the $\Delta$CV-EDP does exceed the predetermined threshold amount, the control system 74 increases the LRL and monitors the average CV-EDP values at the elevated heart/pacing rates associated with the increased LRL (block 360). In one embodiment, the CRM system 10 maintains the LRL at the increased setting for a prescribed time period, and then determines whether a predetermined event has occurred (block 370).

The threshold $\Delta$CV-EDP values for triggering the LRL increase can be determined by the clinician at implantation or thereafter through programming changes based on the patient's history and clinical needs. Additionally, the $\Delta$CV-EDP can be based on any useful measure of CVP changes. For example, in one embodiment, the $\Delta$CV-EDP will be evaluated as a change average CV-EDP value measured as a percentage of the baseline value. Thus, in this example, the control system 74 may be programmed to initiate the LRL increase when the $\Delta$CV-EDP value reaches a predetermined percentage increase over the baseline CV-EDP value, in which case this percentage would represent the programmed threshold value described above. In another embodiment, the $\Delta$CV-EDP may be expressed as an absolute rise, e.g., as measured in mm/Hg, in the average CV-EDP over the baseline CV-EDP. In short, the CRM system 10 provides for broad flexibility in defining the specific operating parameters/thresholds.

Similar to the method 200 discussed above, exemplary predetermined events include the $\Delta$CV-EDP returning to a value equal to or below the programmed threshold value for triggering the LRL increase. Another event that may trigger the reduction in the LRL is the passage of a prescribed time limit for pacing at the elevated rate where the CV-EDP has not fully returned to a value below the programmed threshold. In still another embodiment, the LRL may be reduced upon a detection by the CRM system 10, based on the CV-EDP trend, of worsening hemodynamic conditions.

As shown, if one or more of the predetermined events has occurred, the control system 74 returns the LRL back to its initial setting (block 380). If one or more of the predetermined events has not occurred, in the illustrated embodiment, the control system 74 further increases the LRL and continue to monitor the CV-EDP for a prescribed time period, as indicated by the return arrow to from block 370 to block 360 in FIG. 6. In another embodiment, the control system 74 will maintain the LRL at the initial elevated rate, but will not initiate further increases in the LRL setting (i.e., the return arrow from block 370 to block 360 in FIG. 6 is omitted).

In still other embodiments, other operating parameters may be programmed into the control system 74 of the CRM system 10. In one exemplary embodiment, the control system 74 may be programmed to initiate a predetermined number of LRL increases while not to exceeding a maximum pacing rate limit, e.g., the maximum sensor rate (MSR) or maximum tracking rate (MTR). Thus, for example, the control system 74 may be programmed to increase the LRL up to a rate setting a predetermined margin, e.g., expressed as a percentage of or a number of beats/minute below the MSR/MTR. In short, a range of operating scenarios can be implemented according to the various embodiments of the present invention.

While not shown in FIG. 6, the method 300 further contemplates recalculating the baseline CV-EDP value(s) after completion of the therapy cycle described above (i.e., upon returning the LRL to its initial programmed value). Thus, the method 300 can then be repeated as appropriate.

Thus, the CRM system 10 utilizes hemodynamic performance information based on the output from implanted CVP sensors to diagnose medical conditions, such as the onset of early decompensation resulting from CHF, and to adjust the LRL settings so as to pace the heart at an elevated rate to facilitate removal of fluid accumulated in the patient's cardiopulmonary system as a result of CHF. The CRM system 10 thus advantageously provides a means for diagnosing and treating CHF-related symptoms based on actual patient hemodynamic state information.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of operating an implanted cardiac rhythm management system in a patient, the method comprising:
    applying an electrical stimulus to the patient's heart at a first set of pacing parameters including an LRL setting;
    acquiring a CVP signal from a pressure sensor implanted in a coronary vein of the patient;
    calculating a baseline CV-EDP value from the CVP signal corresponding to a first interval;
    monitoring average CV-EDP values over a predetermined time interval subsequent to the first interval;
    comparing each of average CV-EDP values to the baseline CV-EDP value; determining a difference ($\Delta$CV-EDP) between at least one of the average CV-EDP values and the baseline average CV-EDP value
    automatically increasing the LRL setting in response to said difference ($\Delta$CV-EDP) between at least one of the average CV-EDP values and the baseline average CV-EDP value exceeding a predetermined threshold; and
    subsequently automatically reducing the LRL setting upon detecting a predetermined event.

2. The method of claim 1 wherein the predetermined event includes the $\Delta$CV-EDP returning to below the predetermined threshold.

3. The method of claim 1 wherein the predetermined event is an expiration of a predetermined time period for applying the electrical stimulus at the increased LRL setting.

4. The method of claim 1 wherein the baseline CV-EDP value is a rolling average CV-EDP value over a plurality of cardiac cycles or a predetermined time interval.

5. The method of claim 1 further comprising recalculating the baseline CV-EDP value after reducing the LRL setting upon detecting the predetermined event.

6. The method of claim 1 wherein the predetermined threshold is a programmed percentage change in any of the plurality of average CV-EDP values relative to the baseline CV-EDP value.

7. The method of claim 1 monitoring average CV-EDP values includes generating a CVP waveform based on the CVP signal and calculating an average CV-EDP value over a predetermined interval based on the CVP waveform.

8. The method of claim 1 wherein the automatically increasing the LRL setting includes maintaining the LRL setting at the increased setting for a prescribed time interval.

9. The method of claim 8 further comprising increasing the LRL if the predetermined event is not detected after the prescribed time interval.

10. The method of claim 9 further comprising increasing the LRL up to a prescribed maximum LRL if the predetermined event is not detected after the prescribed time interval.

* * * * *